United States Patent
Jeng et al.

(10) Patent No.: US 9,421,103 B2
(45) Date of Patent: Aug. 23, 2016

(54) LATERAL ANKLE FUSION PLATE SYSTEM AND JIG, AND METHOD FOR USE THEREWITH

(71) Applicant: ORTHOHELIX SURGICAL DESIGNS, INC., Medina, OH (US)

(72) Inventors: Clifford L. Jeng, Ellicott City, MD (US); Jackson R Heavener, Warsaw, IN (US); Mark Myerson, Baltimore, MD (US); Bryan D. Den Hartog, Rapid City, SD (US); Thomas San Giovanni, Coral Gables, FL (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 261 days.

(21) Appl. No.: 13/826,901

(22) Filed: Mar. 14, 2013

(65) Prior Publication Data
US 2014/0107798 A1 Apr. 17, 2014

Related U.S. Application Data

(60) Provisional application No. 61/620,569, filed on Apr. 5, 2012.

(51) Int. Cl.
*A61B 17/80* (2006.01)
*A61F 2/30* (2006.01)
(Continued)

(52) U.S. Cl.
CPC ......... *A61F 2/30749* (2013.01); *A61B 17/1728* (2013.01); *A61B 17/1739* (2013.01); *A61B 17/808* (2013.01); *A61B 17/8061* (2013.01); *A61F 2/4202* (2013.01)

(58) Field of Classification Search
CPC .. A61B 17/80; A61B 17/8061; A61B 17/808; A61B 17/8052; A61B 17/8057; A61B 17/1728
See application file for complete search history.

(56) References Cited

U.S. PATENT DOCUMENTS 4,781,182 A 11/1988 Purnell et al.
7,335,204 B2 * 2/2008 Tornier .............. A61B 17/8061
606/280

(Continued)

FOREIGN PATENT DOCUMENTS

WO 2010/061410 A1 6/2010

OTHER PUBLICATIONS

International Search Reported dated Aug. 19, 2013.
(Continued)

*Primary Examiner* — Zade Coley
(74) *Attorney, Agent, or Firm* — Duane Morris LLP

(57) ABSTRACT

The invention comprises a lateral ankle fusion plate, a jig for use with the fusion plate and a method for ankle fusion of the joints between the tibia, the talus, and the calcaneus. In addition, a separate fusion screw from posterior to anterior through the calcaneal tuberosity into the distal tibia is useful and can be placed using the targeting jig of the invention. The plate includes a C-shaped stirrup portion that wraps the bottom of the calcaneus and is provided with a screw hole for a T-T-C-fusion screw. A C-shaped targeting jig is provided that interfaces with the plate to allow for placement of the calcaneal screw and has an additional attachment for placement of the independent fusion screw so as to avoid impingement with the plate, and plate screws. The invention also relates to a method of surgery that incorporates the use of the plate, the jig and the tibial/talar/calcaneal fusion screw for an arthrodesis of the ankle joint.

25 Claims, 13 Drawing Sheets

(51) Int. Cl.
    *A61B 17/17*     (2006.01)
    *A61F 2/42*     (2006.01)

(56) References Cited

U.S. PATENT DOCUMENTS

| | | | |
|---|---|---|---|
| 7,892,264 B2 | 2/2011 | Sanders et al. | |
| 8,021,402 B2 | 9/2011 | Martin et al. | |
| 8,118,848 B2 | 2/2012 | Ducharme et al. | |
| 8,177,822 B2 | 5/2012 | Medoff | |
| 2003/0055429 A1* | 3/2003 | Ip | A61B 17/8085 606/284 |
| 2004/0116930 A1* | 6/2004 | O'Driscoll | A61B 17/8061 606/281 |
| 2005/0234472 A1 | 10/2005 | Huebner | |
| 2007/0212915 A1* | 9/2007 | Strnad | A61B 17/8047 439/248 |
| 2008/0021452 A1* | 1/2008 | Ducharme | A61B 17/8061 606/60 |
| 2008/0051786 A1* | 2/2008 | Jensen | A61B 17/8057 606/86 A |
| 2008/0269807 A1* | 10/2008 | Simon | A61B 17/746 606/290 |
| 2008/0300637 A1* | 12/2008 | Austin | A61B 17/74 606/290 |
| 2009/0118769 A1* | 5/2009 | Sixto, Jr. | A61B 17/8061 606/280 |
| 2009/0248084 A1* | 10/2009 | Hintermann | A61B 17/8004 606/286 |
| 2010/0057133 A1 | 3/2010 | Simon | |
| 2010/0069973 A1 | 3/2010 | Castaneda et al. | |
| 2010/0217328 A1* | 8/2010 | Terrill | A61B 17/8061 606/286 |
| 2011/0184413 A1 | 7/2011 | Slater | |
| 2011/0213420 A1 | 9/2011 | Medoff | |
| 2011/0245830 A1 | 10/2011 | Zgonis et al. | |
| 2011/0264149 A1 | 10/2011 | Pappalardo et al. | |
| 2011/0295378 A1 | 12/2011 | Bojarski et al. | |
| 2011/0313422 A1* | 12/2011 | Schwager | A61B 17/8061 606/71 |
| 2012/0109215 A1 | 5/2012 | Ducharme et al. | |
| 2012/0109217 A1 | 5/2012 | Perineau et al. | |
| 2012/0215223 A1* | 8/2012 | Chiodo | A61B 17/8061 606/70 |
| 2012/0303033 A1* | 11/2012 | Weiner | A61B 17/151 606/87 |

OTHER PUBLICATIONS

Supplementary European Search Report issued in connection with corresponding European patent application No. EP13773154, Feb. 17, 2016, 9 pages.

* cited by examiner

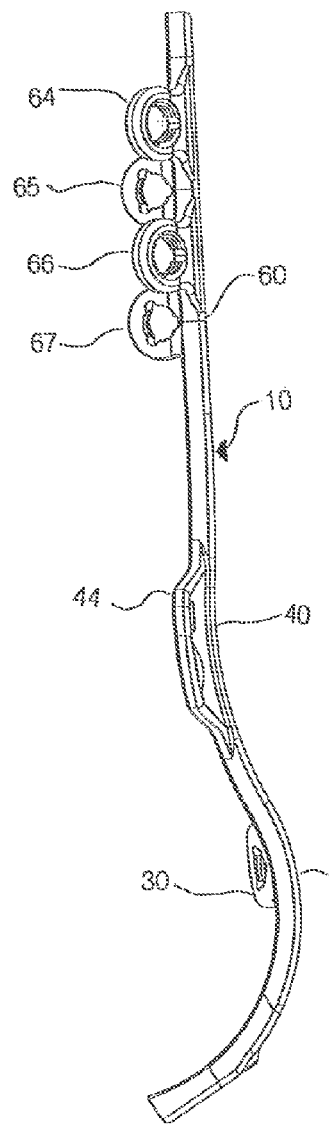
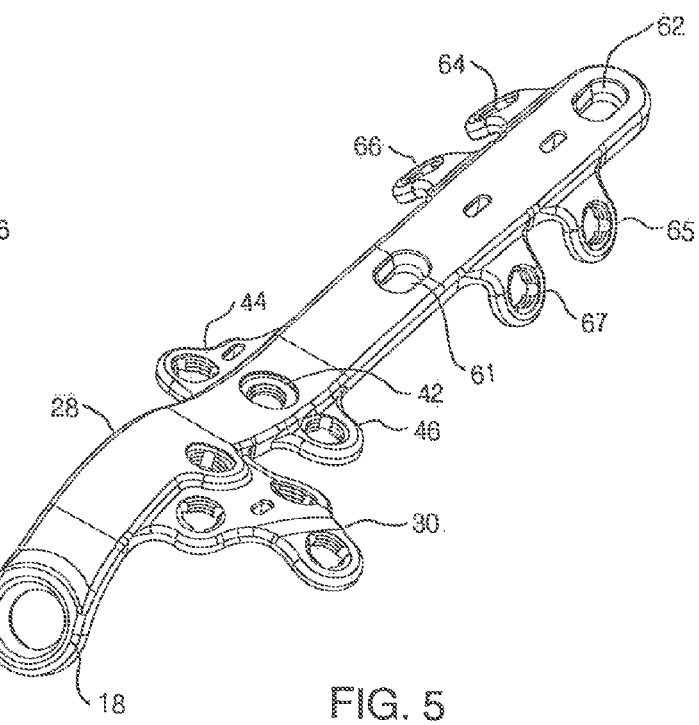
FIG. 3
FIG. 4
FIG. 5

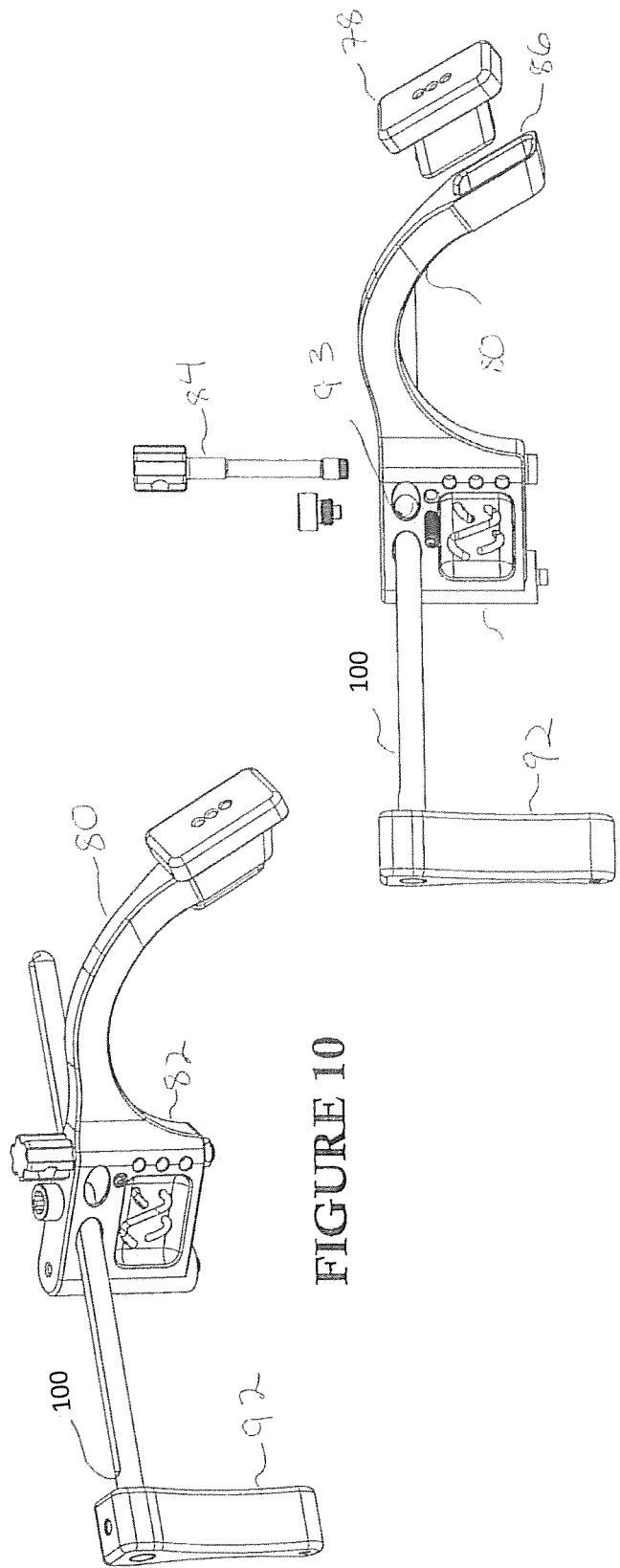

LATERAL ANKLE FUSION PLATE SYSTEM AND JIG, AND METHOD FOR USE THEREWITH

FIELD OF THE INVENTION

The present disclosure relates to an invention which involves an ankle fusion plate system, a jig for use with the fusion plate system and a method for ankle fusion, i.e. arthrodesis, where the joints between the tibia, the talus, and the calcaneus of a human patient can be immobilized using a lateral implant alone, or in combination with a separate fusion screw from posterior to anterior through the calcaneal tuberosity into the distal tibia. The plate includes a C-shaped stirrup portion that wraps the bottom of the calcaneus and is provided with a screw hole for the placement of a relatively vertical screw (i.e., relative to the lower leg, i.e., in the sagittal plane from inferior to superior) through the articular capsule of the talocalcaneal joint and the tibiotalar joint and which secures the calcaneus, the talus and the tibia together. An independent 50-100 mm fusion screw can be used with the lateral plate to augment the immobilization by multiplanar fixation. This screw is placed from the posterior calcaneus at a superiorly extending angle through the talus toward the anterior distal tibia. A C-shaped targeting jig is provided that interlaces with the plate to allow for placement of the calcaneal screw and pivots for placement of the fusion screw so as to avoid impingement with the plate, and plate screws. The invention also relates to a method of surgery that incorporates the use of the plate, the jig and the tibial/talar/calcaneal fusion screw for an arthrodesis of the ankle joint.

BACKGROUND OF THE INVENTION

Despite the importance of a fully functional ankle joint for movement and balance, there are instances in which the pain that can be generated by certain pathologies justify fusion in order to alleviate on-going pain. It is sometimes necessary or desirable to cause fusion or arthrodesis of the primary bones that form the ankle joint, for example, in the case of osteoarthritis, post-traumatic osteoarthritis, ankle arthritis or after failure of total ankle replacement. In this instance given the role of the ankle in allowing for balance and movement, given the high loads to which the ankle joint is subjected, and given the relative lack of soft tissue to cover an implant, it is particularly important that the procedure result in a highly precise placement of the implant and fasteners, as well as a precise and secure joint immobilization.

Prior art devices for use in arthrodesis include wires, screws, plates and intramedullary devices. While such devices exist, each is lacking in providing one or more of the desired precision, stability, fixation, or relative ease of implantation that an orthopedic surgeon desires for such a device.

Thus, it is an object of the present invention is to provide an ankle fusion system and surgical method for implanting an implant in a human ankle, which allows for fusion of the distal end of a tibia, the talus and calcaneus (i.e. the "T-T-C" interface) using a lateral incision to the tibia, talus, fibula and calcaneus region, removing some or all of a fibula in the incision area, attaching the implant to the tibia, talus and calcaneus in a generally central area of the lateral ankle so as to encourage the bones to fuse together. The system includes a lateral plate having a central rail member with fastener holes and preferably including one or more locking holes and/or compression holes. The rail member is planar across its width and includes a slight undulation in the z dimension along the longitudinal axis to accommodate a generalized surface of the distal tibia in the place of the fibula that has been removed. The inferior portion of the plate forms a C-shaped stirrup under the calcaneus and includes at its inferior-most end a screw hole for the placement of a fusion screw, which is advantageously a compression screw of sufficient length to extend through the T-T-C interfaces. The invention further includes a jig, which attaches to the rail to permit a placement of the T-T-C screw that avoids impingement with the other plate fasteners, and also that is at the optimal angle to achieve fusion. The fusion is augmented by the use of the separate (i.e. which does not cooperate directly with the plate) fusion screw that angles up through the calcaneus, talus to the anterior portion of the distal tibia.

Apart from the calcaneal stirrup segment, the rail member has a first lateral segment that abuts the calcaneus, a second lateral segment that abuts the talus, and a third lateral segment that abuts the tibia. The rail member further includes tabs or wing portions on each of the calcaneal segment, the talar segment, and the tibial segment. The calcaneal wing includes a plurality of fastener holes, i.e., preferably a triangular arrangement of three, and a slot for placement wires, such as k-wires, while a tab extends from the anterior edge of the rail member in the talar segment substantially in opposition to a slightly posterior talar tab, each of which has a single locking screw hole. The anterior talar wing also has a slot for a guide wire. The tibial segment has stepped tabs, which wrap around the tibia on each of the anterior and posterior sides with each tab including a single locking screw hole. This segment also includes compression slots below and above the stepped tabs. The talar segment of the plate also includes a central locking hole that can be used for a screw as well as to position and fasten the targeting jig relative to the plate.

The calcaneal jig in accordance with the present invention has a large C-shaped end, which can be pivoted in relation to the central talar hole, and having a drill guide to position a second fusion screw in a posterior portion of the calcaneus. Examples of the conditions for which the present invention are useful include arthritis with or without associated deformity of the ankle and subtalar joint, rheumatologic arthritis and deformity, severe ankle and subtalar arthrosis, talar collapse, avascular necrosis of the talus, hindfoot deformity, stage 4 flatfoot and/or Charcot neuroarthropathy and/or deformity. The invention can be used for both a tibiotalocalcaneal and a tibiocalcaneal (TC) arthrodesis where a partial or total talectomy is necessary.

SUMMARY OF THE INVENTION

An object of the present disclosure is therefore to provide a system for ankle fusion which improves upon the shortcomings of the prior art and to provide novel systems and methods for immobilizing the joints between the tibia, talus and the calcaneus of a human patient that makes it possible to perform arthrodesis under good operating conditions while also making it possible to obtain bone fusion that is particularly stable, strong, precise, and comfortable for the patient.

Another object of the present disclosure is to provide novel systems and methods for immobilizing the joints between the tibia, talus, and the calcaneus of a human patient that is particularly successful under all conditions of bone quality or pathology.

Another object of the present disclosure is to provide novel systems and methods for immobilizing the joints between the tibia, talus, and the calcaneus of a human patient that is relatively easy to implant, that avoids the most congested areas of ligament and tendon involvement, and that result in reliable bone fusion.

The objects assigned to the present disclosure are achieved by systems and methods as described herein for immobilizing the joint between the tibia and the talus of a human patient. The system and method of the present disclosure comprise a lateral T-T-C fusion plate system that includes a rail member having a tibial segment, a talar segment and a calcaneal segment which extends into a C-shaped segment that cradles the inferior portion of the calcaneus, and cooperates with a compression screw that extends upwardly through the calcaneus, the talus and into the tibia. A C-shaped targeting jig is provided that facilitates the placement of the calcaneal fusion screw, and which can be pivoted to allow an independent posterior screw to be angled in the T-T-C joint so as to avoid impingement with the fastener screws.

BRIEF DESCRIPTION OF THE DRAWINGS

FIG. 3 is a side view of the plate of FIG. 1 taken from the posterior side;

FIG. 4 is an end view of the plate of FIG. 1 taken from the proximal end (from an anatomical perspective);

FIG. 5 is an end perspective view of the plate of FIG. 1 taken from the proximal end;

FIG. 10 is a side perspective of the targeting jig from FIG. 8;

FIG. 11 is a side view of the targeting jig from FIG. 8 with an exploded view of the pivoting screw, fusion screw axis and pilot drill guide;

DETAILED DESCRIPTION OF THE INVENTION

Figures 1, 2:
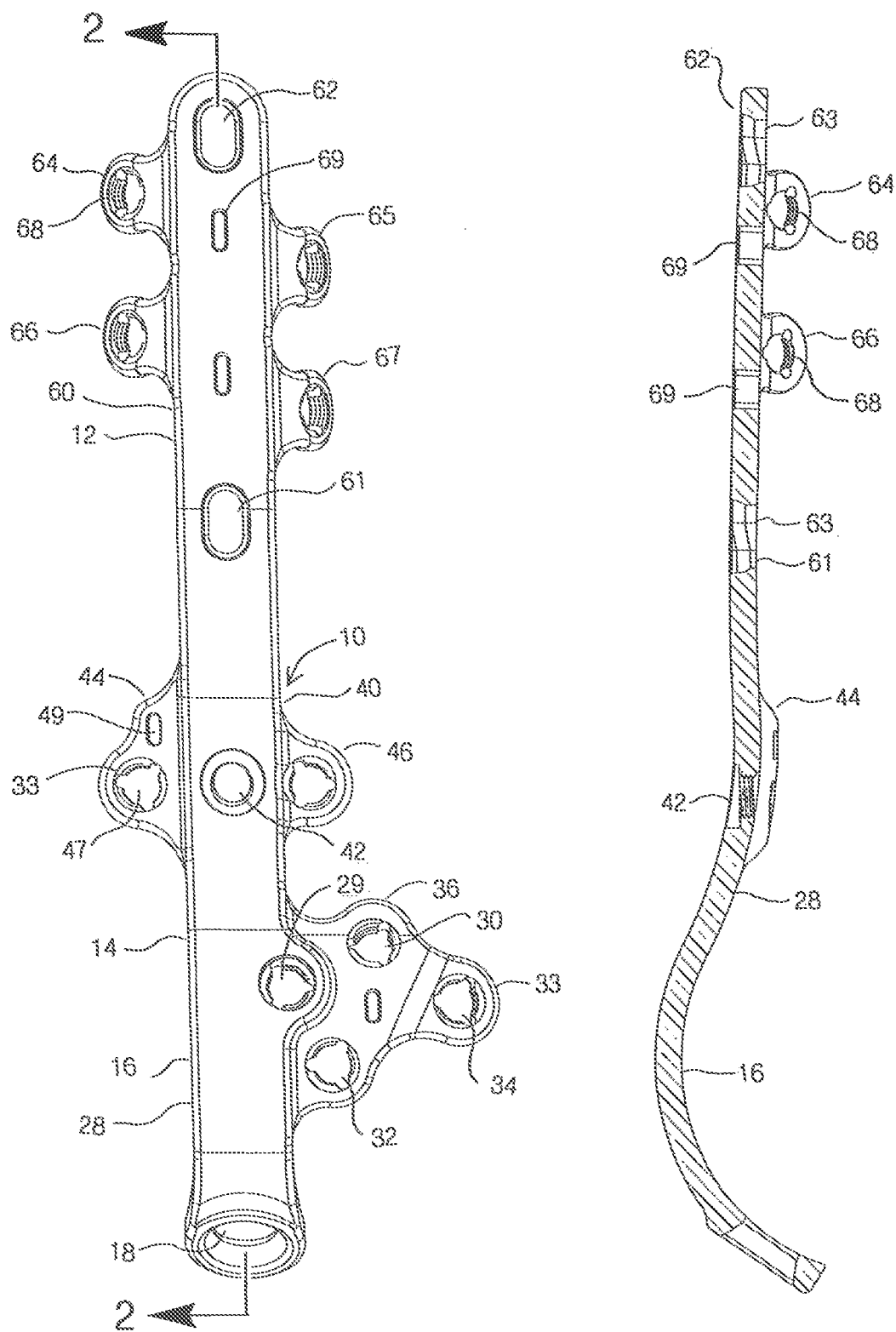
FIG. 1 is a front view of a left T-T-C fusion plate of the present invention.
FIG. 2 is a cross section of the plate of FIG. 1 taken along line 2-2.
Figure 6:
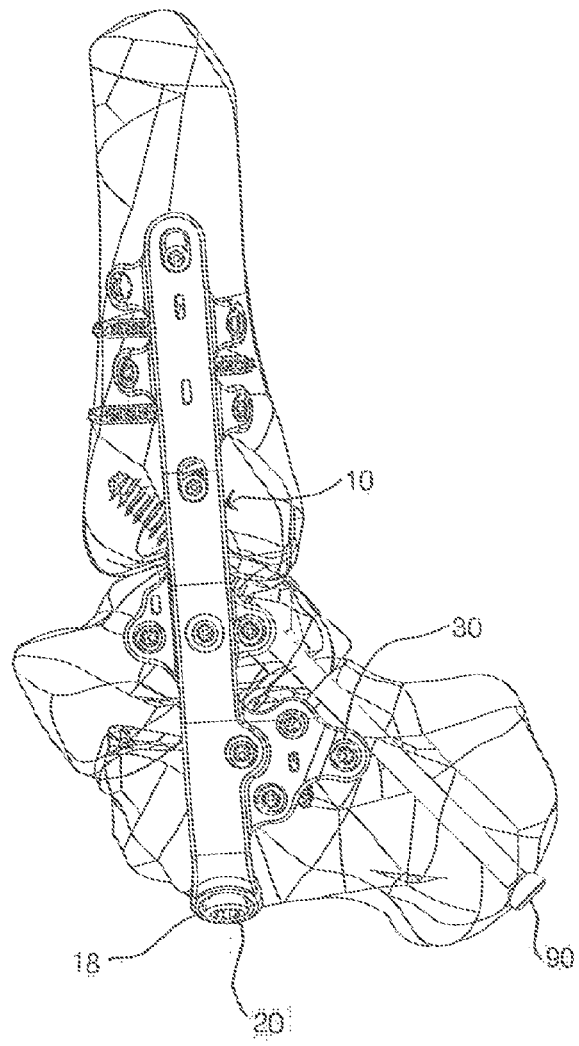
FIG. 6 is a lateral view of the plate of FIG. 1 with screws in position on an ankle.
Figure 7:
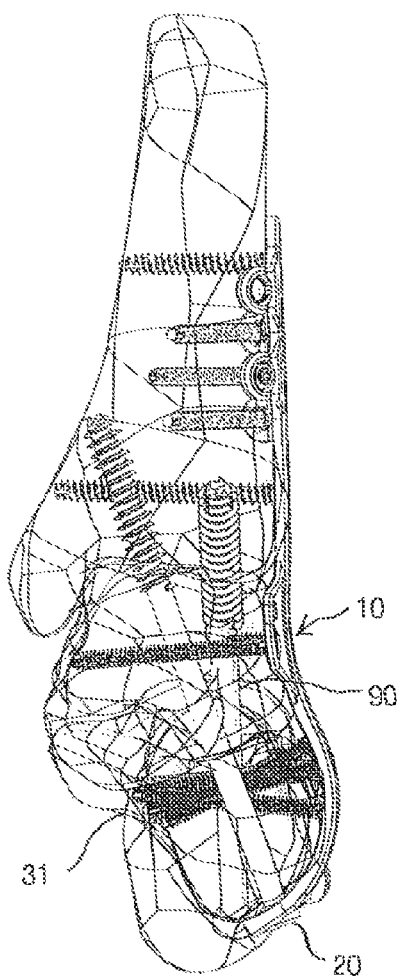
FIG. 7 is an anterior view of the plate of FIG. 1 with screws in position on an ankle.
Figure 8:
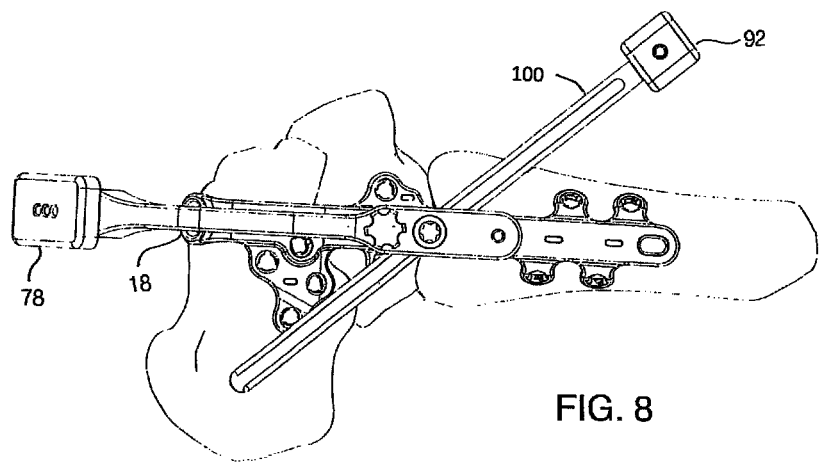
FIG. 8 is a lateral view of the plate of FIG. 1 in position on an ankle, and including the jig for placement of the calcaneal screw through the screw hole in the calcaneal stirrup segment of the plate.
Figure 9:
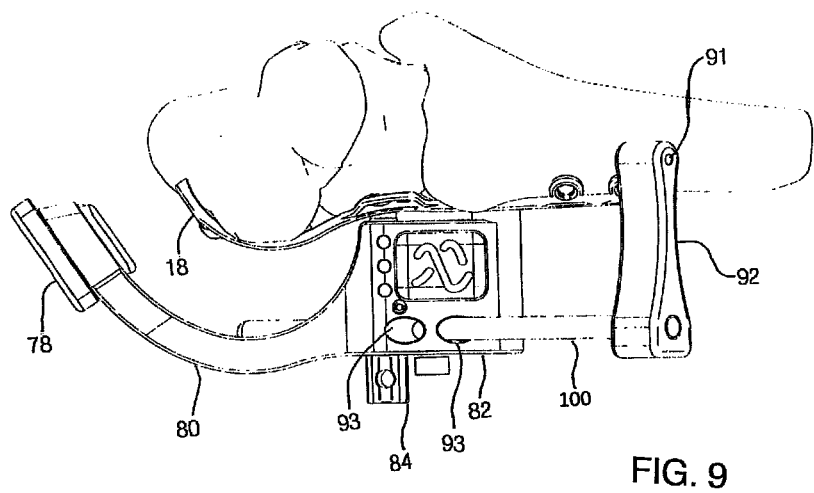
FIG. 9 is an anterior view of the plate of FIG. 1 in position on an ankle and including the jig for placement of a separate fusion screw through the T-T-C joint.
Figure 12:
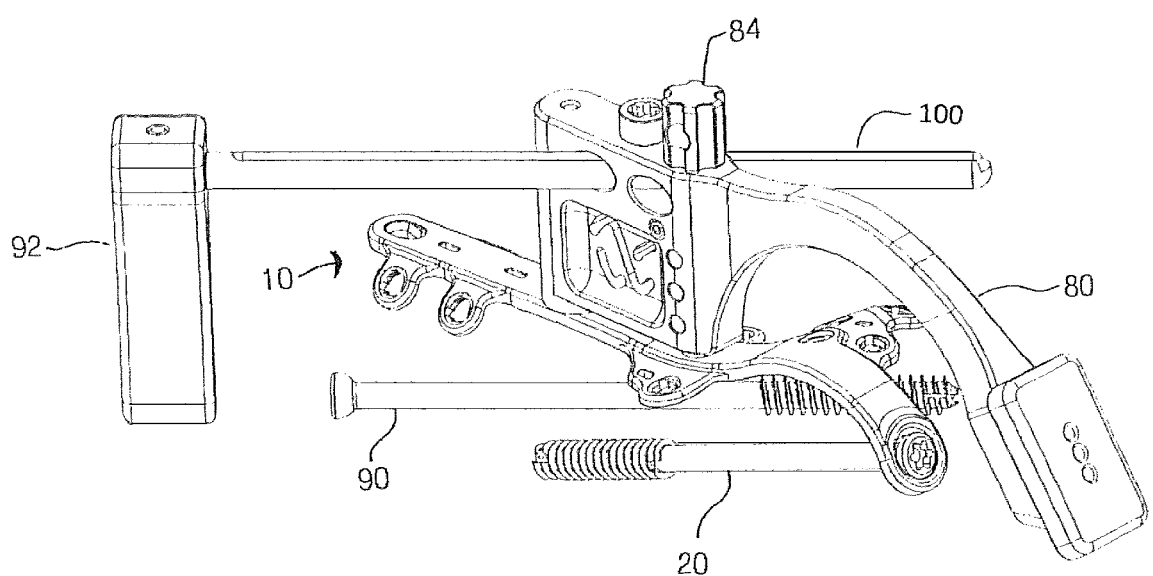
FIG. 12 is a side perspective of the targeting jig showing the placement of the fusion screws.
Figure 13:
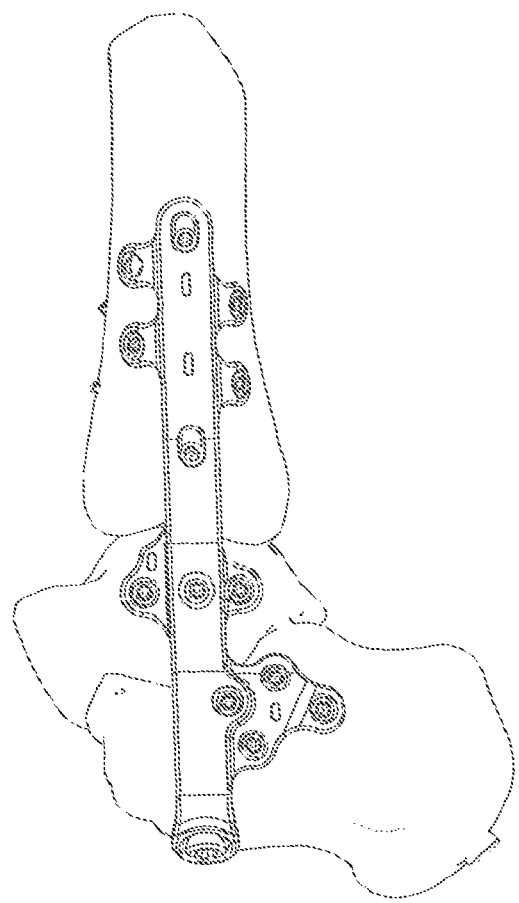
FIG. 13 is a lateral (front) view of the plate and screws in position on an ankle.

FIG. 1 illustrates a side view of a lateral ankle fusion plate 10 in accordance with the present invention. The plate 10 has a central rail member 12 with a first segment 14 that abuts the calcaneus. This segment has a C-shaped portion or stirrup 16 (i.e. along the longitudinal axis) that wraps under the inferior surface of the calcaneus. The curve is a compound curve that forms about 70°+/−10°, or more preferably 5°, of a circle and having a radius of from about 0.74 to about 0.84 inch+/−0.1 inch such that the terminal screw hole 18 in the calcaneal position is about 1.8 inch +/0.25 inch from the posterior screw hole in the talar segment. The plate has a length from the axis of the central screw hole of the talar segment in the tibial terminus of about 3 inches+/−025 inch.

The central axis 18' of the screw hole 18 forms an angle of from about 30° to about 60°, and preferably at about 40° to about 50°, and most preferably at about 42° to about 47° to a medial line in that second or talar segment of the plate (shown in FIG. 2). This hole receives a compression screw 20 that is from about 50 to about 100 mm and preferably from about 70 to about 90 mm long. Advantageously, this is a lag screw, or a compression screw having a distal set of threads 22 abutting a non-threaded region 23 and a head 24 that interfaces with the plate 10 to avow the screw 20 to draw the plate into the bone and to draw the bones of the T-T-C together. In addition, it is preferable that this screw includes a cannulation (not shown).

The first longitudinal or calcaneal segment 14 also includes a first laterally oriented (i.e., relative to the body) section 28, which has a posteriorly placed locking hole 29 and a posterior calcaneal wing 30. This wing includes three locking holes wherein an intermediate hole 34 opposes the locking hole 29 and locking holes 32 and 36 are located closer to the longitudinal axis of the rail portion of the plate, but are respectively more inferior and superior to the intermediate locking hole 34. Specifically, the locking holes of the present invention are internally threaded and correspond to the threads which are external to the head of a locking screw 31 used within the locking holes of the invention. Of course, it should be understood that other means of locking may be used, such as variable locking assemblies. The locking holes are also shown as including a triad of channels 33 which provide for the seating of a drill guide to permit the placement of a pilot hole that will accommodate the locking screw that is placed through the corresponding hole The second longitudinal or talar segment 40 includes a central locking hole 42 and an anterior tab or wing 44 and a posterior tab 46 that respectively extend anteriorly and posteriorly from the side of the rail portion. The posterior tab 46 includes a single locking hole 48, while the anterior tab includes a locking hole 47 and a slot 49 for a guide wire where the locking hole is aligned along the longitudinal axis of the plate with the central locking hole 42.

The third longitudinal or tibial segment of the plate 60, includes a first and a second compression slot 61,62 each having lateral edges 63 that define a shoulder which angles toward the bone facing side of the plate in the direction of the calcaneal segment. The tibial segment also includes two pairs of tabs 64,66 and 65,67 having respective locking holes 68 and located on each of the anterior and the posterior sides of the plates where the tabs alternate in position along the length of the rail beginning with a first tab on the posterior side and ending with an anterior tab on the proximal (i.e., at the tibial) end of the plate. Further, these tabs in the tibial segment are angled away from the rail member so as to wrap the tibia. Thus, these tabs extend at a smaller angle than the tabs of the first and second longitudinal segments which may be substantially co-planar with the rail portion of the plate to which they are attached. The second compression slot 62 is located in the proximal end of the plate 10. This section also includes slots 69 for guide wires.

The rail member 12 is planar across its width and includes a slight undulation in the z dimension along the longitudinal axis to accommodate a generalized surface of the distal tibia in the place of the fibula that has been removed. The inferior portion of the plate forms a C-shaped stirrup under the calcaneus and includes at its inferior most end, a hole 18 for a T-T-C fusion screw 20. This screw 20 can be placed using the drill guide section 78 of a C-shaped jig member 80 having a body 82, which attaches by threading an attachment member 84 into the central locking screw hole 42 of the talar segment 40 of the rail 12 to permit a placement of the T-T-C fusion screw 20 that avoids impingement with the other plate fasteners, and also that is at the optimal angle to achieve fusion. As is illustrated in FIG. 11, once a pilot hole is drilled for the fusion screw, the screw can be implanted with the jig in place through an opening 86 in the end of the jig. In addition the jig has an arm 100 with a guide 92 having a hole 91 for a pilot drill and journaled in a left or a right hole 93 in the body 82 of the jig to define an optimal angle 92 for a separate fusion screw 90. The fusion is augmented by the separate (i.e. which is does not cooperate directly with the plate) fusion screw 90 that angles up through the calcaneus, talus to the medial portion of the tibia superior to the medial malleolus. This separate screw 98 is of a similar length as the screw 20, i.e., from about 50 to about 100 mm long, and preferably from about 65 to about 80 mm long, and is a compression screw which may advantageously be threaded along a distal portion of the screw, and lacking threads in an area adjacent the head of the screw.

A surgical technique in accordance with the invention is described as follows:

Surgical Approach

A lateral transfibular approach to the ankle and hindfoot is used for the arthrodesis and correction of deformity. Although this distal fibulectomy may slightly devascularize the lateral ankle, this technique calls for a fibulectomy for exposure and plate application. This approach is particularly useful in the setting of severe deformity in either the sagittal or coronal plane or both.

Exposure

The incision is made vertically, directly over the fibula, extending down distally over the sinus tarsi toward the inferior aspect of the calcaneus. The sural nerve must be identified and then retracted inferiorly and posteriorly with the peroneal tendons. It may be necessary to retract the nerve and tendons anteriorly depending on the soft tissue, scarring and deformity. In some cases it is acceptable to cut the peroneal tendons, particularly where they are already torn, a common finding with a chronic varus hindfoot and ankle deformity.

Once the peroneal tendons are retracted posteriorly, the calcaneofibular and anterior talofibular ligaments are cut exposing the entire distal fibula. A fibulectomy is now performed. It is ideal to use the fibula for bone graft, and this can either be morcellized following an osteotomy with a saw, or removed by harvesting the entire fibula. If a distal fibulectomy is performed, harvesting the entire distal 4 cm with a small acetabular reamer can be done. The reamer is applied with pressure to the fibula, and is used to completely denude and decorticate the bone leaving a shell of the inner cortex behind yielding copious cancellous graft. For application of the plate, it is necessary to remove the distal 8 cm of the fibula, and following use of the reamer, the remaining fibula is cut more proximally with a saw and discarded.

The lateral aspect of the calcaneus must be exposed to visualize the plantar lateral margin of the calcaneus for apposition of the plate. The approach to preparation of the joint surfaces depends on the need for preservation of the anatomy and the presence of deformity. If there is minimal deformity present, then it is preferable to use a chisel to thoroughly denude the ankle and subtalar joints. One should be careful not to remove excess bone laterally from either joint since this will tilt the arthrodesis into valgus. Nevertheless, maintaining the contour of both the ankle and subtalar joint is an option. If deformity is present, the joint surfaces can be prepared by making flat cuts with a saw.

A wide fan shaped saw blade is used protecting the soft tissue on the posterior and anterior ankle with malleable retractors. The saw is oriented perpendicular to the tibial shaft and the tibial plafond cut, removing about 2 mm in the center of the joint increasing to about 5 mm anteriorly and 7 mm posteriorly depending on the presence of osteophytes in the anterior and posterior ankle. Then while holding the ankle in neutral dorsiflexion and 5-7 degrees of valgus, a parallel flat cut is made on the dome of the talus removing approximately 5 mm of bone.

Depending on the ability to obtain a plantigrade foot and the ankle in a neutral position, the medial malleolus may be cut obliquely through a separate incision on the medial ankle. This cut is made obliquely to exit at the level of the tibial plafond. This osteotomy will permit easy translation of the talus under the tibia in any direction to facilitate deformity correction.

Once the foot is in a neutral position under the tibia, the neutral position should be verified under fluoroscopy and provisionally maintained by two crossing guide wires. The lateral flare of the distal tibia will require ostectomy with a chisel or osteotomy to allow the plate to sit flush on the bone surface.

Surgical Technique

Figure 14:
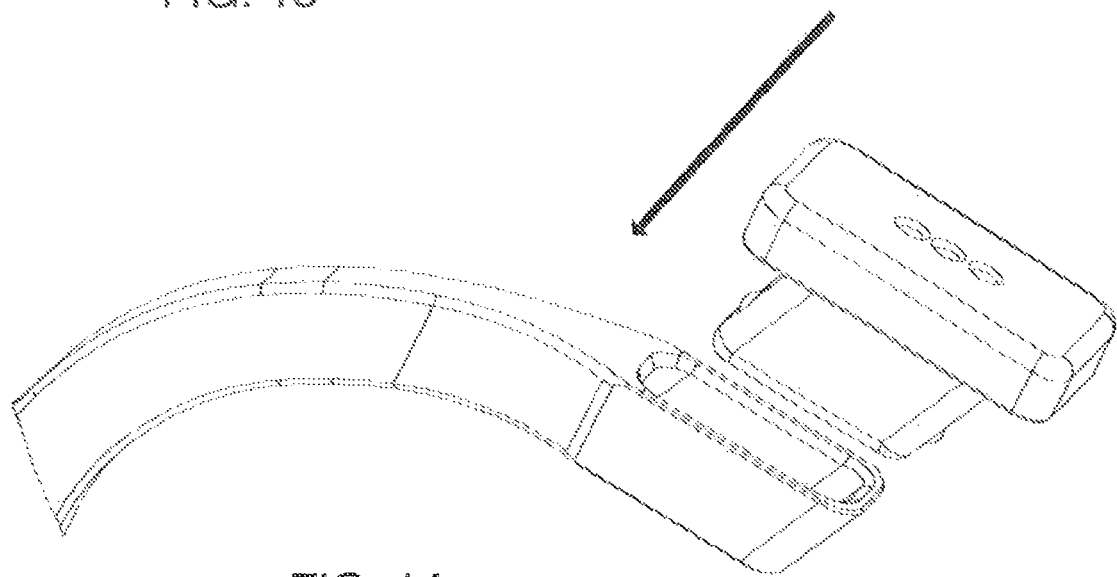
FIG. 14 is an illustration of the first step in use of the assembly of the parts of a drill guide in accordance with the present invention.
Figure 15:
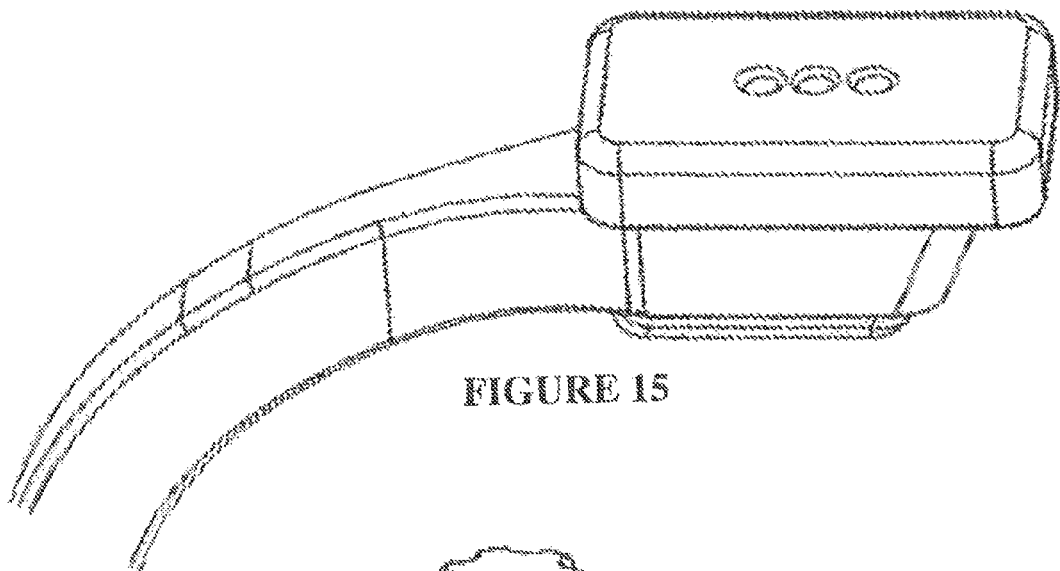
FIG. 15 is an illustration of the assembly of FIG. 14.

Step 1: Assemble the primary targeting guide by inserting the K-wire guide insert into the distal head of the guide as shown in FIG. 14 and as assembled in FIG. 15.

Figure 16:
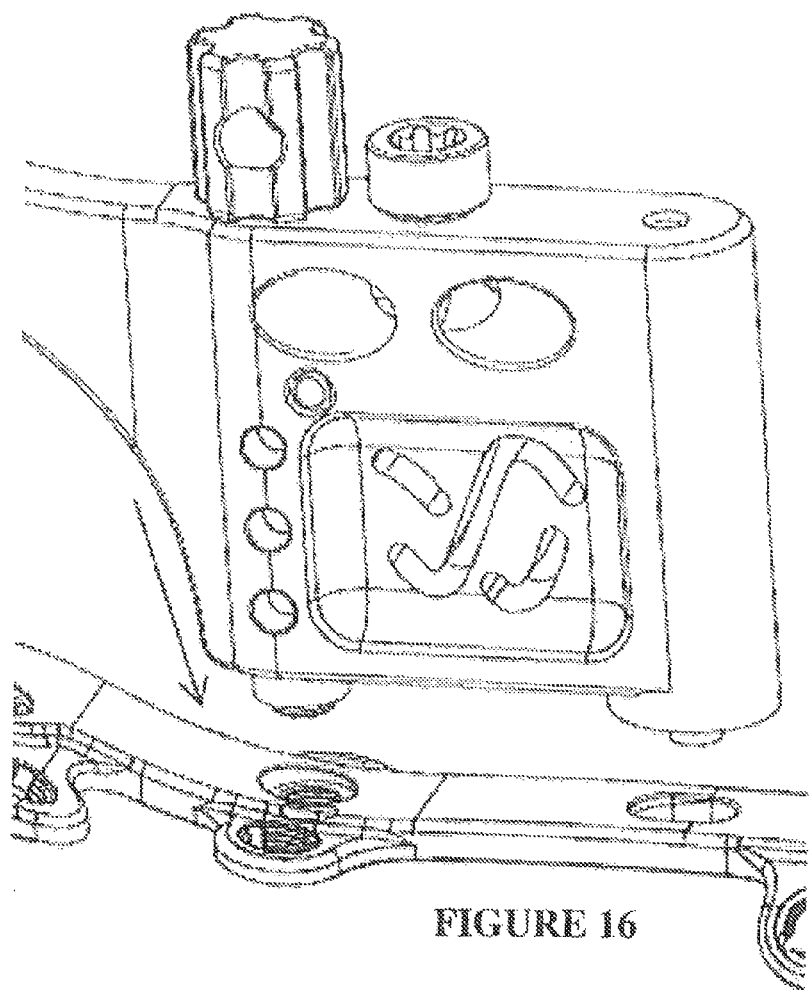
FIG. 16 is an illustration of the assembly of the drill guide with the bone plate in accordance with the present invention.
Figure 17:
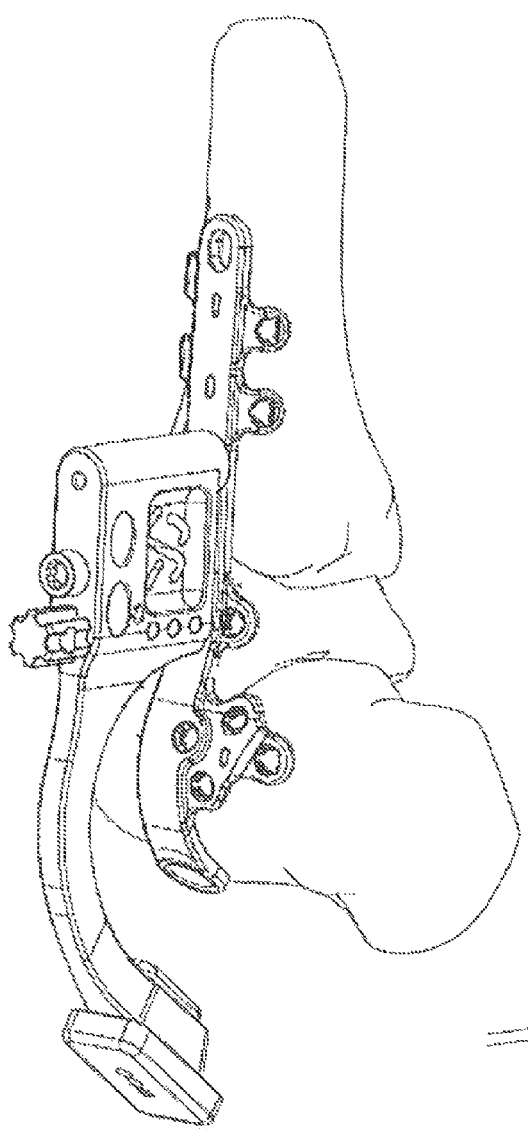
FIG. 17 is illustration of the drill guide in position on the bone plate in accordance with the present invention.

Step 2: Attach the lateral ankle fusion plate (depending on the operative side) by threading the insert into the central locking hole on the plate as shown in FIGS. 16 and 17. The guide can be used as a handle to aid in plate placement.

Step 3: Insert the plate deep into the peroneal tendons (the tendons can be excised if torn) in order to avoid compromising either skin closure or ultimate peroneal function. The distal portion of the jig should sit outside of the incision and wrap under the inferior aspect of the calcaneus. This guide will later facilitate the insertion of a 7.0 mm screw from the calcaneus into the tibia.

Step 4: The plate can now be provisionally fixed by a combination of k-wires and olive wires. When placing k-wires within the k-wire slots, place them in the most proximal portion of the slot. This will allow for compression in subsequent steps as the relative motion of the plate will allow translation from distal to proximal during compression.

Figure 18:
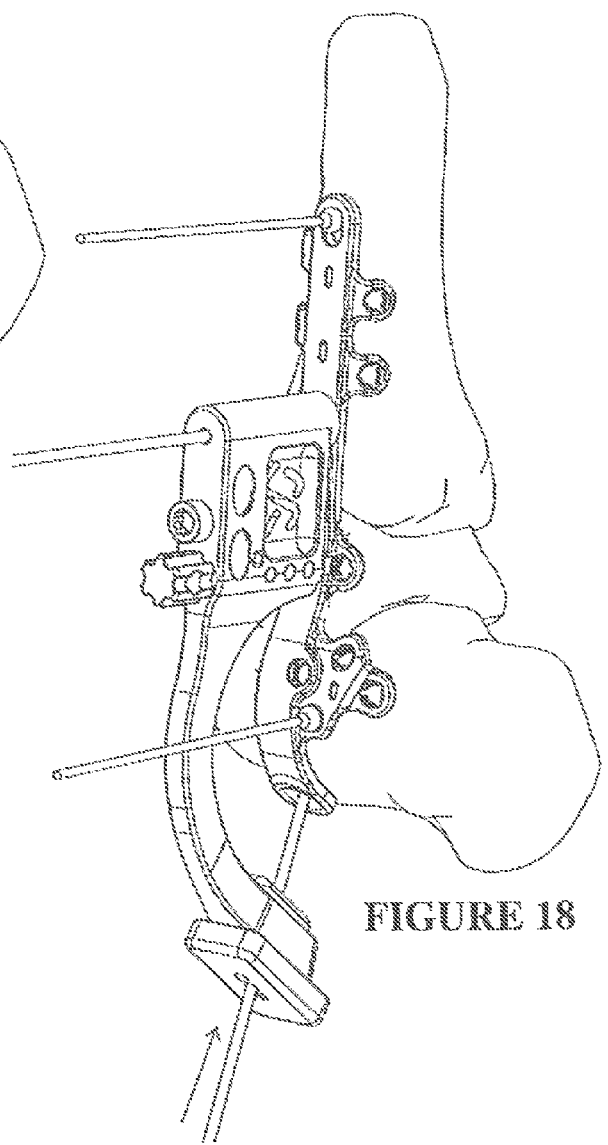
FIG. 18 is an illustration of the drill guide and bone plate with guide wires in position.

Step 5: Insert a 2.3 mm k-wire through one of the holes in the K-wire guide insert as shown in FIG. 18. The angle of the k-wire will depend on the height of the talus but should be inserted so as to maximize the cortical capture of the distal tibia. The targeting guide has graduations of +0°, +5° and +10° (corresponding to relative angles of 23°, 18° and 13° between the k-wire and the plate). Select the angle that best and most accurately captures the distal medial tibia and confirm under fluoroscopy.

Step 6: Following fluoroscopic verification of the k-wire position, remove the K wire Guide Insert by snapping it out of the primary targeting jig and pulling it over the guide wire. Use a 4.7 mm cannulated drill bit to perforate the calcaneus, talus and the cortical edge of the distal tibia.

Figure 19:
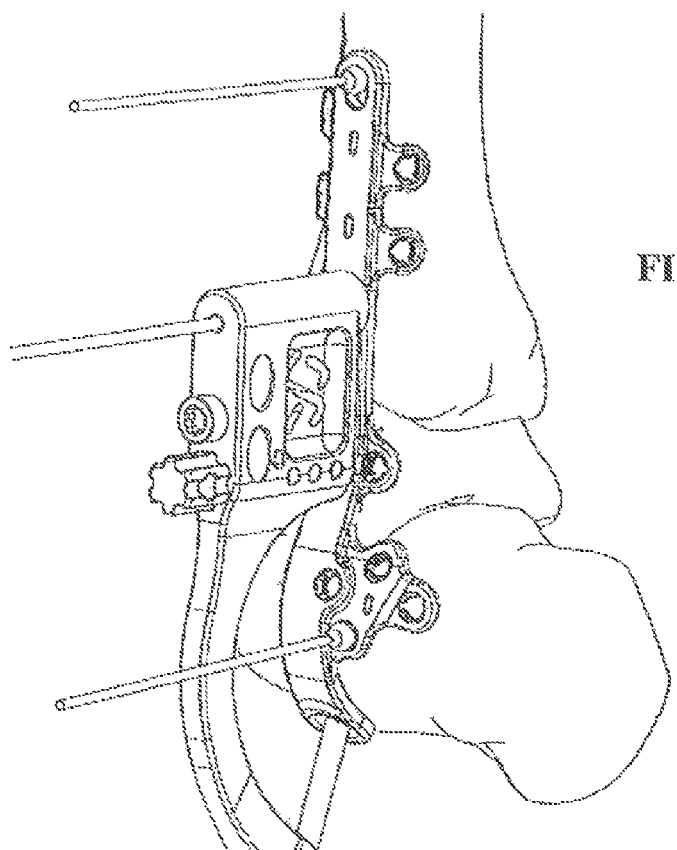
FIG. 19 is an illustration of the assembly of FIG. 17 used for the insertion of a fusion screw through the distal end of the plate.

Step 7: Measure using the provided depth gauge. Using the appropriate driver, insert the correct length 7.0 mm short thread screw to compress both the ankle and the subtalar joints as is shown in FIG. 19.

Optional Secondary 7.0 mm Screw Insertion: The Secondary Targeting Guide can be used if a second 7.0 mm screw is desired. This guide will allow placement of a 7.0 mm screw through the center of the calcaneus and will prevent collision with the primary screw. The guide is designed to introduce the guide wire into either the posterior calcaneus or anterior tibia, depending on surgeon preference. The diameter of the secondary targeting guide rod is the same as the 7.0 mm screws and can be used to approximate the angle and position of the posterior 7.0 mm screw.

Figure 20:
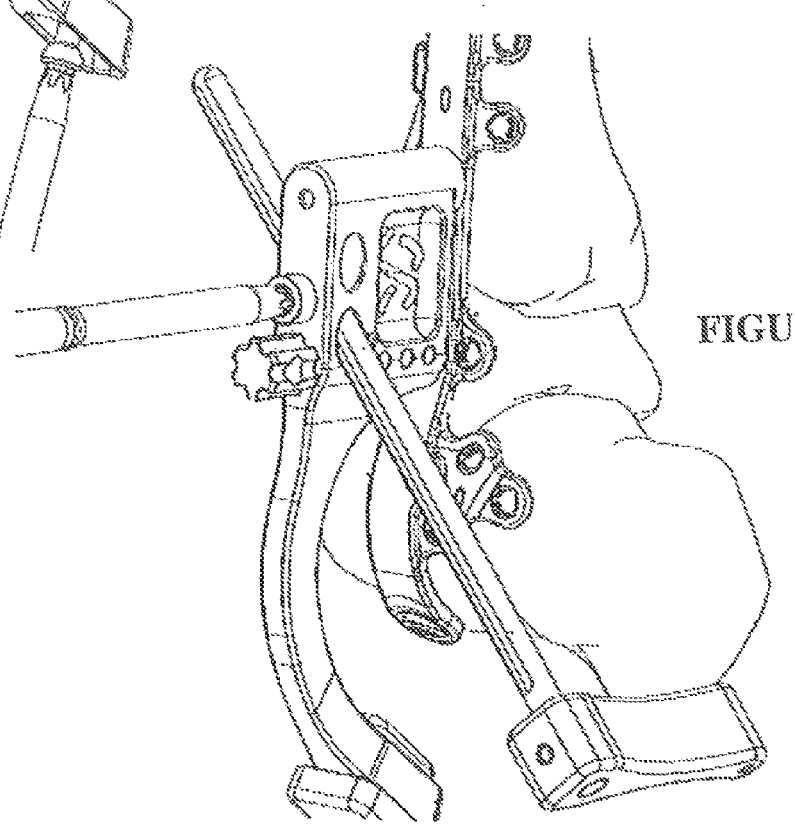
FIG. 20 is an illustration of showing the addition of a further drill guide for an independent fusion screw.

Step 8: Insert the secondary targeting guide through the hole corresponding to the operative side in the primary targeting guide as shown in FIG. 20. Adjust the rod to the desired position and fix in place by tightening the lock nut using the 7.0 mm driver.

Figure 21:
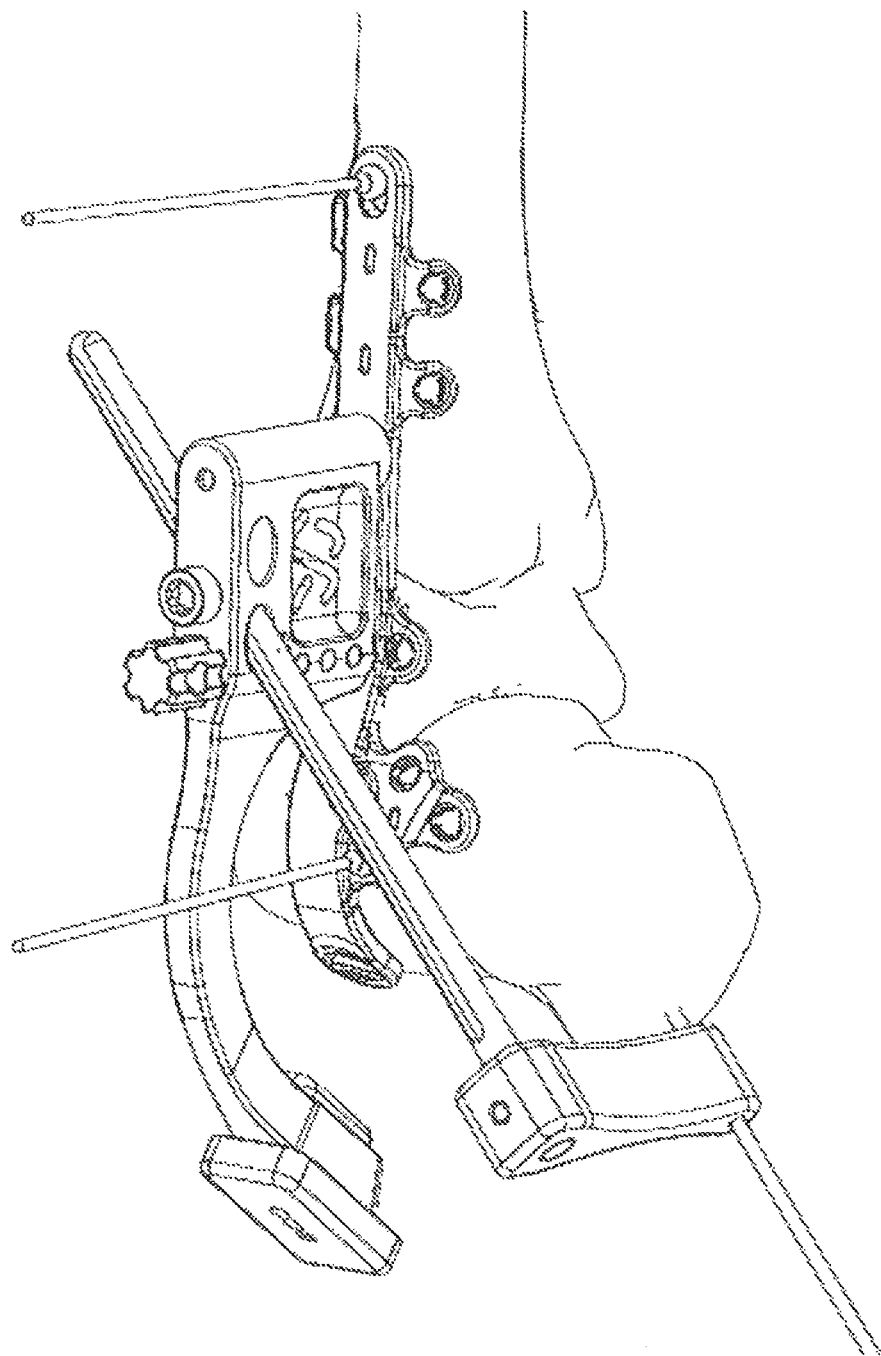
FIG. 21 is an illustration of the assembly of FIG. 18 showing an additional guide wire for the fusion screw.

Step 9: Insert a 2.3 mm k-wire through the guide hole in the secondary targeting guide head as shown in FIG. 21. Drive the wire into the calcaneus (or tibia) and across the joint line and confirm under fluoroscopy.

Step 10: Following fluoroscopic verification of the position of the k-wire, remove the entire targeting guide assembly and use the 4.7 mm cannulated drill bit to perforate the calcaneus, talus and the anterior cortical edge of the distal tibia.

Step 11: Measure using the provided depth gauge and insert the correct length 7.0 mm short thread screw to further compress both the ankle and the subtalar joints.

Cortical Screw Insertion: The remaining locking screw holes may be filled with either Fixed-Angle Locking Screws or Non-Locking Screws as appropriate depending on the need for stability and fixation. Fixed angle drill guides should be used to drill for both screw types.

Step 12: To drill for the remaining screws, use either a drill guide such as a fixed drill guide which threads into the locking hole to provide the proper angle for drilling or a keyed quick insertion drill guide having lobes on the tip of the guide which align with the lobes in the threaded hole and is pressed into the plate while drilling to ensure proper alignment.

Step 13: Using the 2.4 mm drill bit drill to the desired depth.

Figure 22:
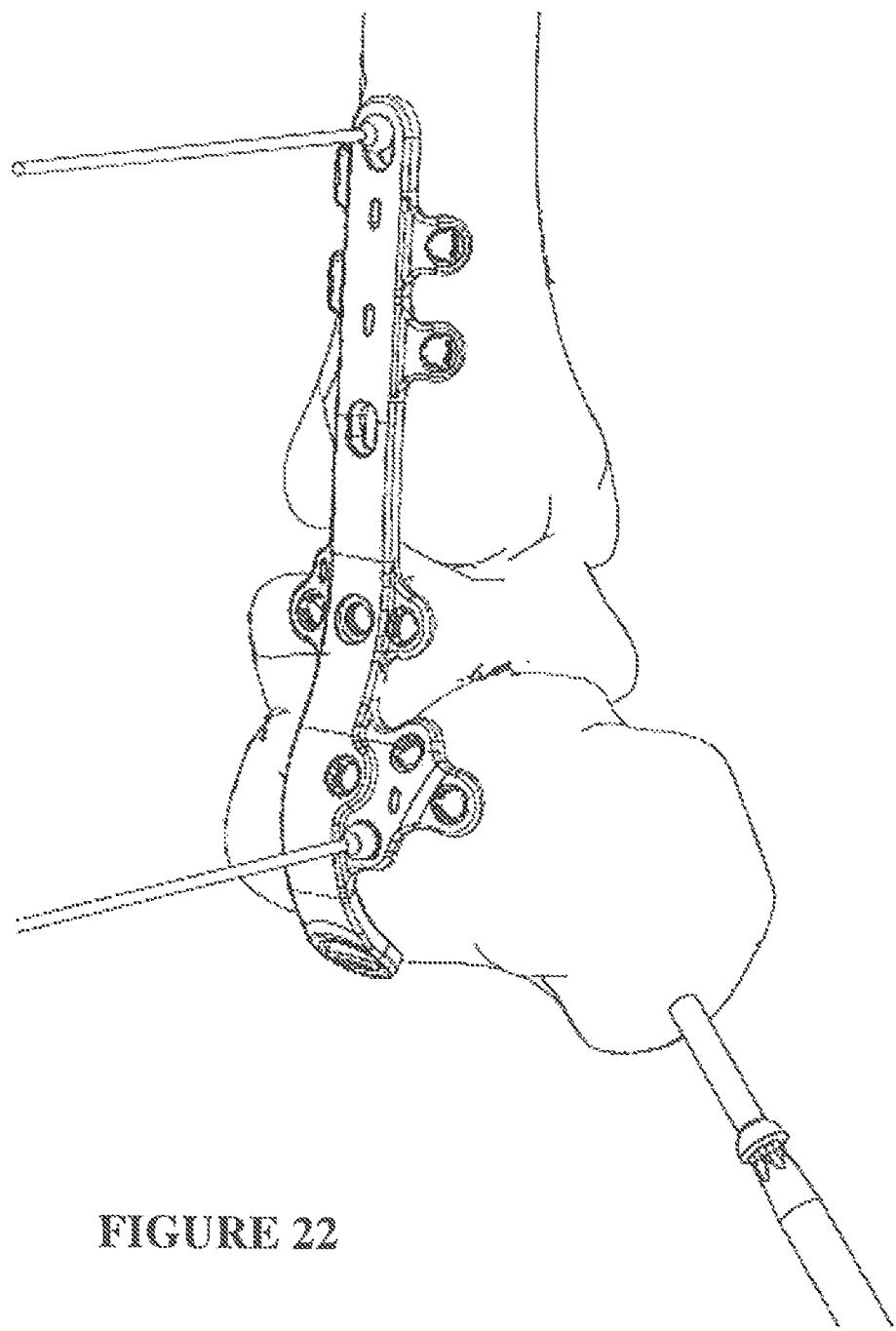
FIG. 22 is a posterior view showing the placement of the fusion screw in accordance with the invention.
Figure 23:
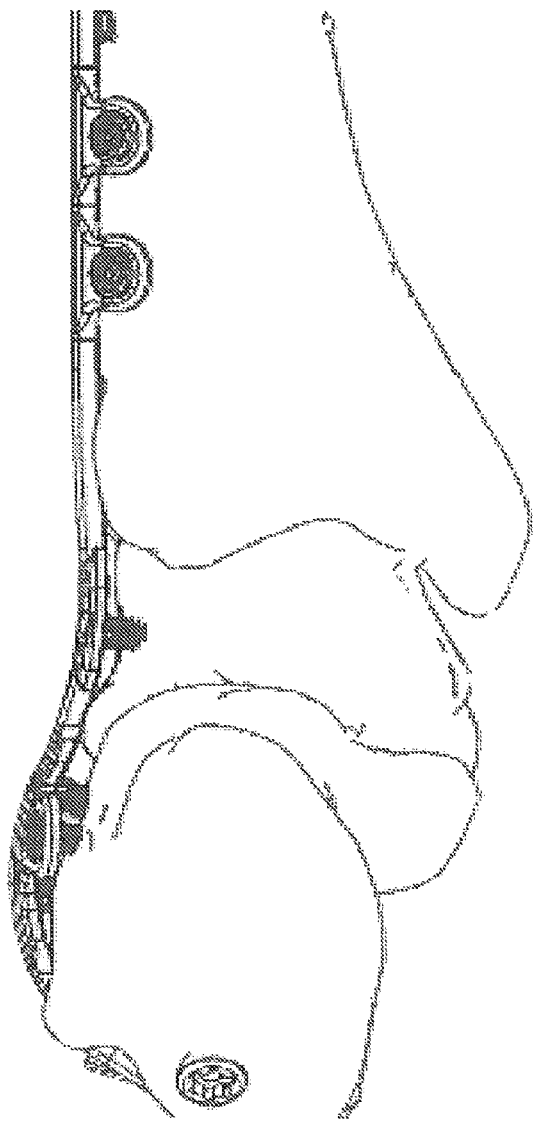
FIG. 23 is a posterior view of the assembly of the plate and fusion screws in accordance with the present invention.
Figure 24:
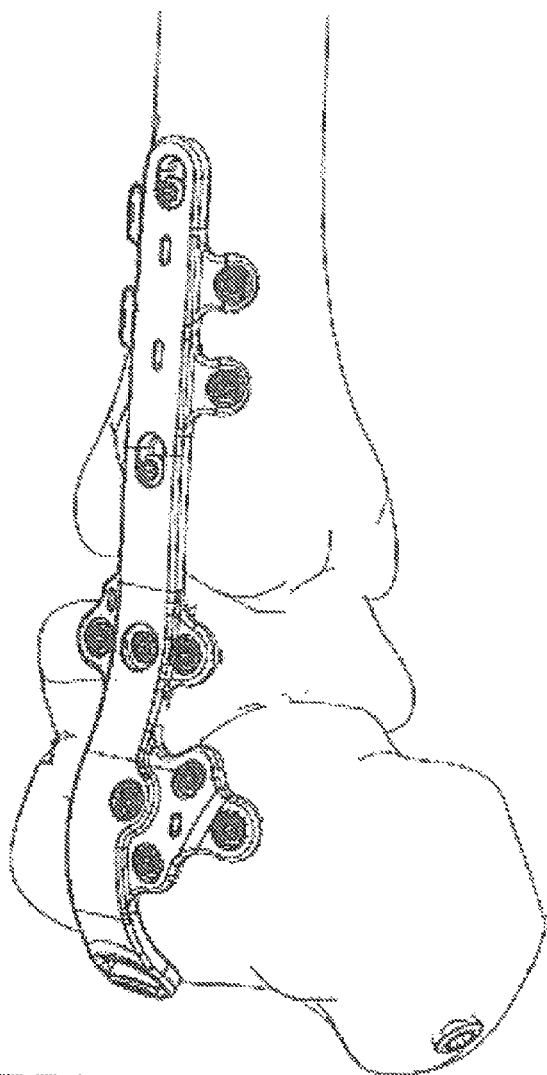
FIG. 24 a side and posterior view of the assembly of the plate and fusion screws in accordance with the present invention.

Step 14: Measure using the provided depth gage and insert the appropriate length screw using the appropriate driver. FIGS. 22, 23 and 24 illustrate the plate, and compression screws placed for ankle fusion in accordance with the method of the present invention.

While in accordance with the patent statutes the best mode and preferred embodiment have been set forth, the scope of the invention is not limited thereto, but rather by the scope of the attached claims.

What is claimed is:

1. A fusion implant system for use on an ankle of a patient comprising at least one locking screw having a threaded distal portion and an externally threaded head portion, at least one fusion screw having a fusion screw head portion, and a plate extending along a longitudinal axis comprising a rail member having a Z-direction and a first segment which is a calcaneal segment including a C-shaped stirrup in cross-section in the direction of the longitudinal axis that curves in a compound curve that forms 70°+/−10° of a circle of a radius having a radius of from 0.74 inch to 0.84 inch +/−0.1 inch and a top surface configured to face away from a tibia and the rail member undulates in the Z-direction as a portion of the compound curve whereby the C-shaped stirrup of the calcaneal segment is configured to wrap under an inferior surface of a calcaneus and has a distal hole that receives the fusion screw and cooperates with the fusion screw head portion for holding the plate relative to the calcaneus in use, the plate having a second segment configured for attachment to a talus and further including at least one internally threaded hole that cooperates with the externally threaded head portion of the locking screw to form a locked angle relation between the locking screw and the plate, and the plate having a third segment configured for attachment to a lateral section of the tibia.

2. A fusion implant system as set forth in claim 1 wherein the second segment has at least one tab which extends from the rail member and which includes the internally threaded hole for the locking screw.

3. A fusion implant system as set forth in claim 1 wherein the rail member has a top surface configured to face away from the tibia and opposing long sides and the second segment includes at least two tabs which include an internally screw threaded hole for a locking screw and which extend from either opposing long side of the rail member at an angle relative to the top surface of the rail member.

4. A fusion implant system as set forth in claim 3 wherein the plate includes at least two sets of tabs wherein each tab includes an internally threaded screw hole for the locking screw and wherein each set has two tabs which are longitudinally offset and which extend from either opposing long side of the rail member at an angle relative to the externally facing surface of the rail member.

5. A fusion implant system as set forth in claim 4 further including a compression screw having a minor diameter and a compression head and wherein the rail member includes at least one compression slot having a longitudinal length and a lateral width and a lateral shoulder that angles downward to drive compression in the direction of the longitudinal length as the compression head of the compression screw cooperates with the shoulder.

6. A fusion implant system as set forth in claim 5 further including a guide wire having a diameter that is smaller than the minor diameter of the compression screw and wherein the rail member includes at least one slot which has a lateral width that is larger than the diameter of the guide wire and that is smaller than the lateral width of the compression slot and has a longitudinal length in the direction of the longitudinal length, and the longitudinal length of the slot is greater than the lateral width.

7. A fusion implant system as set forth in claim 4 wherein the plate further includes a third set of two tabs that extend from either long side of the rail member and which each include an internally threaded screw hole for the locking screw, and the third set of tabs is intermediate the first two sets of tabs and the calcaneal segment.

8. A fusion implant system as set forth in claim 7 wherein said plate further includes a posterior long side and a posterior wing that extends from the posterior long side of the plate and which has three internally threaded screw holes for a locking screw.

9. A fusion implant system as set forth in claim 8 wherein the posterior wing also includes at least one slot for a guide wire which has a longitudinal length and a lateral width that is larger than the diameter of the guide wire and that is smaller than the lateral width of the at least one compression slot and the longitudinal length of the slot is greater than the lateral width.

10. A fusion implant system as set forth in claim 7 further including an attachable jig having a body and an arm that has a drill guide and wherein the plate includes an internally threaded central hole through which the drill guide is attached to the plate for alignment of the fusion screw through the distal hole.

11. A fusion implant system as set forth in claim 10 further including an independent second fusion screw and the jig has an attachment for the placement of the second fusion screw such that an impingement between the second fusion screw and the at least one locking screw is inhibited.

12. A fusion implant system for fusion of a joint between a tibia, a talus, and a calcaneus and comprising at least one locking screw having a threaded distal portion and an externally threaded head portion, at least one fusion screw having a fusion screw head portion, and a plate extending along a longitudinal axis comprising a rail member having a Z-direction and a first segment which is a calcaneal segment including a C-shaped stirrup in cross-section in the direction of the longitudinal axis that curves in a compound curve and a top surface configured to face away from the tibia and the rail member undulates in the Z-direction as a portion of the compound curve whereby the C-shaped stirrup of the calcaneal segment is configured to wrap under an inferior surface of the calcaneus and has a distal hole that receives the fusion screw and cooperates with the fusion screw head portion in use, the plate having a second segment configured for attachment to the talus and further including at least one internally threaded hole that cooperates with the externally threaded head portion of the locking screw to form a locked angle relation between the locking screw and the plate, and the plate having a third segment configured for attachment to a lateral section of the tibia.

13. A fusion implant system as set forth in claim 12 wherein the second segment has at least one tab which extends from the rail member and which includes the internally threaded hole for the locking screw.

14. A fusion implant system as set forth in claim 12 wherein the rail member has opposing long sides and the second segment includes at least two tabs which include an internally screw threaded hole for a locking screw and which extend from either opposing long side of the rail member at an angle relative to the externally facing surface of the rail member.

15. A fusion implant system as set forth in claim 12 wherein the plate includes at least two sets of tabs wherein each tab includes an internally threaded screw hole for the locking screw and wherein each set has two tabs which are longitudinally offset and which extend from either opposing long side of the rail member at an angle relative to the externally facing surface of the rail member.

16. A fusion implant system as set forth in claim 12 wherein said plate further includes a posterior long side and a posterior wing that extends from the posterior long side of the plate and which has three internally threaded screw holes for a locking screw.

17. Proposal A fusion implant system for fusion of a joint between a tibia, a talus, and a calcaneus and comprising at least one locking screw having a threaded distal portion and an externally threaded head portion, at least one fusion screw having a fusion screw head portion, and a plate extending along a longitudinal axis comprising a rail member and a first segment which is a calcaneal segment including a C-shaped stirrup in cross-section in the direction of the longitudinal axis that curves in a compound curve whereby the C-shaped stirrup of the calcaneal segment is configured to wrap under an inferior surface of the calcaneus and has a distal hole that receives the fusion screw and cooperates with the fusion screw head portion for holding the plate relative to the calcaneus in use, the plate having a second segment configured for attachment to the talus and further including at least one internally threaded hole that cooperates with the externally threaded head portion of the locking screw to form a locked angle relation between the locking screw and the plate, and the plate having a third segment configured for attachment to a lateral section of the tibia, the plate further including a compression screw having a minor diameter and a compression head and wherein the rail member includes at least one compression slot having a longitudinal length and a lateral width and a lateral shoulder that angles downward to drive compression in the direction of the longitudinal length as the compression head of the compression screw cooperates with the shoulder.

18. A fusion implant system as set forth in claim 17 wherein the second segment has at least one tab which extends from the rail member and which includes the internally threaded hole for the locking screw.

19. A fusion implant system as set forth in claim 17 wherein the rail member has a Z-direction and a top surface configured to face away from the tibia and the rail member undulates in the Z-direction as a portion of the compound curve.

20. A fusion implant system as set forth in claim 17 wherein the rail member has a top surface configured to face away from the tibia and opposing long sides, the plate includes at least two sets of tabs wherein each tab includes an internally threaded screw hole for the locking screw and wherein each set has two tabs which are longitudinally offset and which extend from either opposing long side of the rail member at an angle relative to the top surface of the rail member.

21. A fusion implant system for fusion of a joint between a tibia, a talus, and a calcaneus and comprising at least one locking screw having a threaded distal portion and an externally threaded head portion, at least one fusion screw having a fusion screw head portion, and a plate extending along a longitudinal axis comprising a rail member and a first segment which is a calcaneal segment including a C-shaped stirrup in cross-section in the direction of the longitudinal axis that curves in a compound curve whereby the C-shaped stirrup of the calcaneal segment is configured to wrap under an inferior surface of the calcaneus and has a distal hole that receives the fusion screw and cooperates with the fusion screw head portion for holding the plate relative to the calcaneus in use, the plate having a second segment configured for attachment to the talus and further including at least one internally threaded hole that cooperates with the externally threaded head portion of the locking screw to form a locked angle relation between the locking screw and the plate, and the plate having a third segment configured for attachment to a lateral section of the tibia and the fusion implant system further including an attachable jig having a body and an arm that has a drill guide and wherein the plate includes an internally threaded central hole through which the drill guide is attached to the plate for alignment of the fusion screw through the distal hole.

22. A fusion implant system as set forth in claim 21 wherein the second segment has at least one tab which extends from the rail member and which includes the internally threaded hole for the locking screw.

23. A fusion implant system as set forth in claim 21 wherein the rail member has a Z-direction and a top surface configured to face away from the tibia and the rail member undulates in the Z-direction as a portion of the compound curve.

24. A fusion implant system as set forth in claim 23 wherein the rail member has opposing long sides and the second segment includes at least two tabs which include an internally threaded screw hole for a locking screw and which extend from either opposing long side of the rail member at an angle relative to the top surface of the rail member.

25. A fusion implant system as set forth in claim 21 wherein the rail member has a first and a second opposing long side and a top surface configured to face away from the tibia, the plate includes at least two sets of tabs wherein each tab includes an internally threaded screw hole for the locking screw and wherein each set has two tabs which are longitudinally offset and which extend from either the first or the second opposing long side of the rail member at an angle relative to the top surface of the rail member.

* * * * *